United States Patent
Brown et al.

[11] Patent Number: 5,980,498
[45] Date of Patent: Nov. 9, 1999

[54] HYGIENIC SALIVA COMPENSATION DEVICE

[75] Inventors: Carrie Brown, Dallas; Jack Atkinson, Southlake, both of Tex.; Janet H. Allaire, Charlotteville, Va.; Eric Frische, Plano, Tex.

[73] Assignee: Innovative Human Services, Inc., Dallas, Tex.

[21] Appl. No.: 09/012,936

[22] Filed: Jan. 24, 1998

Related U.S. Application Data

[60] Provisional application No. 60/038,444, Feb. 19, 1997.

[51] Int. Cl.⁶ .................................................. A61M 1/00
[52] U.S. Cl. ........................................... 604/327; 600/573
[58] Field of Search ............................. 604/35, 176, 147, 604/149, 313, 315, 316, 317, 319, 322, 327; 600/573, 578, 579, 582; 4/258, 267, 144.1

[56] References Cited

U.S. PATENT DOCUMENTS

| | | | |
|---|---|---|---|
| 4,114,605 | 9/1978 | McGhee et al. | 128/2 F |
| 4,201,212 | 5/1980 | Bradley | 128/275 |
| 4,635,488 | 1/1987 | Kremer | 73/864.72 |
| 4,768,238 | 9/1988 | Kleinberg et al. | 4/258 |
| 4,813,931 | 3/1989 | Hauze | 604/54 |
| 4,817,632 | 4/1989 | Schramm | 128/769 |
| 4,834,110 | 5/1989 | Richard | 128/760 |
| 5,045,074 | 9/1991 | Satterfield et al. | 604/317 |
| 5,050,616 | 9/1991 | Wolff et al. | 128/760 |
| 5,110,557 | 5/1992 | Brown et al. | 422/101 |
| 5,143,087 | 9/1992 | Yarkony | 128/780 |
| 5,260,031 | 11/1993 | Seymour | 422/101 |
| 5,268,148 | 12/1993 | Seymour | 422/101 |
| 5,380,492 | 1/1995 | Seymour | 422/101 |
| 5,393,496 | 2/1995 | Seymour | 422/101 |
| 5,494,646 | 2/1996 | Seymour | 422/101 |
| 5,720,299 | 2/1998 | Theodoru | 128/760 |

*Primary Examiner*—Ronald Stright
*Assistant Examiner*—David J. Cho
*Attorney, Agent, or Firm*—Gardere & Wynne, L.L.P.; John W. Montgomery

[57] ABSTRACT

A portable saliva compensation device is provided with a portable carrying case holding a vacuum pump, and a portable power supply for providing power to vacuum pump. An electrical control circuit is connected to the portable power supply and the pump. A saliva collection device is positioned at or below a user's mouth for collecting excess saliva and conveying it to a hollow tube connecting between the saliva collection device and the vacuum pump. A saliva detection switch in the saliva collection device is coupled to the electrical control circuit to activate the vacuum pump when saliva is detected in the saliva collection device. This draws the saliva from the collection device through said hollow tube and into a collection reservoir.

27 Claims, 10 Drawing Sheets

HYGIENIC SALIVA COMPENSATION DEVICE

RELATED APPLICATIONS

This application is a continuation in part and conversion of provisional application filed under 37 C.F.R. § 1.53(b)(2), Provisional Patent Application No. 60/038,444, filed Feb. 19, 1997, upon which Applicant relies for priority and which is incorporated herein by reference for all purposes.

TECHNICAL FIELD OF THE INVENTION

The present invention relates to a device for use by individuals having conditions resulting in excessive saliva, improper swallowing functions or other conditions or disorders resulting in uncontrolled drooling. Particularly this relates to a portable hygienic saliva compensation device and method.

BACKGROUND OF THE INVENTION

Drooling is abnormal for people beyond the age of toddlers. For some people with a variety of neurological conditions, drooling is a chronic problem which cannot be remedied by standard intervention methods. There is no definitive research data on the number of people with drooling problems, but the literature estimates that ten percent (10%) of all people with cerebral palsy have unwanted drooling. Individuals with conditions such as head injury, Amyotropic Lateral Sclerosis, and other degenerative neurological diseases can also have a drooling problem.

Previously, there has not been a device for reliable collection of saliva overflow during normal activities of a person with a drooling problem. Without a truly portable and convenient apparatus for the collection of saliva, accurate data related to this problem cannot be easily obtained. Not only would a device be beneficial for people with excess saliva overflow but also reliable collection of saliva overflow is essential for determining the effectiveness of various intervention strategies. Such a device could also be useful as a research tool for physicians and other clinicians in their research to determine the effectiveness of different behavioral, pharmaceutical, and surgical techniques and intervention in dealing with this problem. Moreover, a device useful for clean, safe hygiene, and research, and a training tool to assist in teaching people better behavioral techniques for swallowing and other saliva compensation activities is desirable and has not previously been provided.

SUMMARY OF THE INVENTION

Applicants' invention addresses many of the foregoing needs by providing a modularized, assisted technology hygienic saliva compensation device which is portable by the user and which the user can operate to clean his or her lips and chin of unwanted saliva.

It is the object of the present invention to provide a portable hygienic saliva compensation device. Such a device is desirably discreet, aesthetically acceptable to the user, quiet and reliable.

It is the further object of the invention to provide a hygienic saliva compensation device which is modularized and portable so that it can be carried by the user in a backpack, or fanny pack, or attached to a wheelchair or moveable from one chair to another or from one table to another.

It is the further object of the present invention to provide a device which functions as a vacuum for saliva overflow, collects saliva drool for disposal and/or measurement purposes.

It is the object of the present invention to provide a saliva compensation device which is hygienic and easy to clean, simple for users and for care givers to operate, is nonirritating to the skin, and helps reduce odor problems often associated with excessive drooling.

It is the further object of the present invention to comfortably accommodate natural movements of the user including head, neck, torso, and body movements.

It is the further object of the present invention to provide a saliva compensation device which is designed for conducting research and also for training users to swallow, including variable timing devices and a flexible, embedded cuing system.

It is the further object of the present invention to provide a device useful for clinicians and researchers to determine differences in the amount of drool collected due to different types of clinical or physical intervention by monitoring the amount of saliva overflow collected in a container.

It is an object of the present invention to provide integrated software and hardware in a saliva compensation device to collect data for later analysis on a variety of variables, including natural activities of the user, the number and type of cues given to the user, the number of times and the duration that the vacuum pump is activated. The software and hardware work together to determine and to indicate when the drool collection container or reservoir reaches a full condition.

It is further an object to provide a device with capabilities of being preprogrammed with a computer, of recording operations data in a portable unit, of providing a convenient downloading for analysis in a personal computer through a data communication port, such as an RS-232 serial port, a parallel port, or an infrared communication port.

It is another object to provide a portable device having a programmable, integrated circuit (PIC) capable of receiving downloaded programming instructions for operation, cuing, monitoring of device functions, monitoring of physiological conditions and physical actions of a user, uploading and downloading of instructions from software or another machine, such as a personal computer (PC), is advantageous for research, teaching, and controlling r compensating for excessive salivation.

It is the further object of the present invention to provide an electro mechanical computerized device using various molded silicone parts, molded plastic parts, flexible tubing, flexible wiring, a lightweight pumping unit, a portable power source, and a premanufactured or injection-molded carrying case for holding electronics, batteries, pumps, containers and other components in a portable unit. The modular construction preferably allows for the selection of one or more of three types of collection units. The device is selectably useable and programable with clinical, teaching and research software.

In one embodiment the device may be manufactured in a configuration primarily for use by the buyer with the basic pump, collection unit and carrying case. The essential user unit would preferably include capabilities of accepting up to two of three types of collection units. The user would typically be provided with a shirt unit and either a face unit or a wrist collection unit. Both automatic activation and user switch activation is provided. The unit may have a switch or a combination of switches. Types of switches include a user switch to turn the pumping unit "on" and "off," an automatic resistance sensor to detect the presence or absence of saliva in a collector, a programable "time-out" function to turn on at a predetermined interval to automatically turn on the pumping unit for a predetermined time. The absence of saliva in the collector may turn the pump off or a preselected pumping duration can automatically turn the pump off. The time-out function may be linked to a sensor of physical activity, such as swallowing, to reset the timer or to otherwise alter the automatically-timed pumping activation. Interconnection of any or all of the pump activation mechanisms with optional swallowing detectors is useful for determining whether the pumping is required or whether the pumping duration can be reduced because the user has recently swallowed.

In a second embodiment a clinical saliva compensation unit is provided with a configureable pump unit having multiple input and output connectors to electronic control circuitry. The multiple input and output connectors are convenient and useful for training and research. An onboard Programable Integrated Circuit or PIC is programmable using a PC and data transfer technology. A user can be monitored and evaluated by a clinician and a software module can be provided for data collection and storage. The data can be transferred to other computer devices such as PCs for training and/or for research. Advantageously, programming can be uploaded to the PIC from a clinician's PC and data can be collected and downloaded to the PC from onboard data collection modules.

DESCRIPTION OF THE DRAWINGS

These and other objects and advantages will be more fully understood with reference to the following detained description, claims and drawing figures in which like numerals represent like elements and in which:

DETAILED DESCRIPTION OF THE PREFERRED EMBODIMENTS

Figure 1:
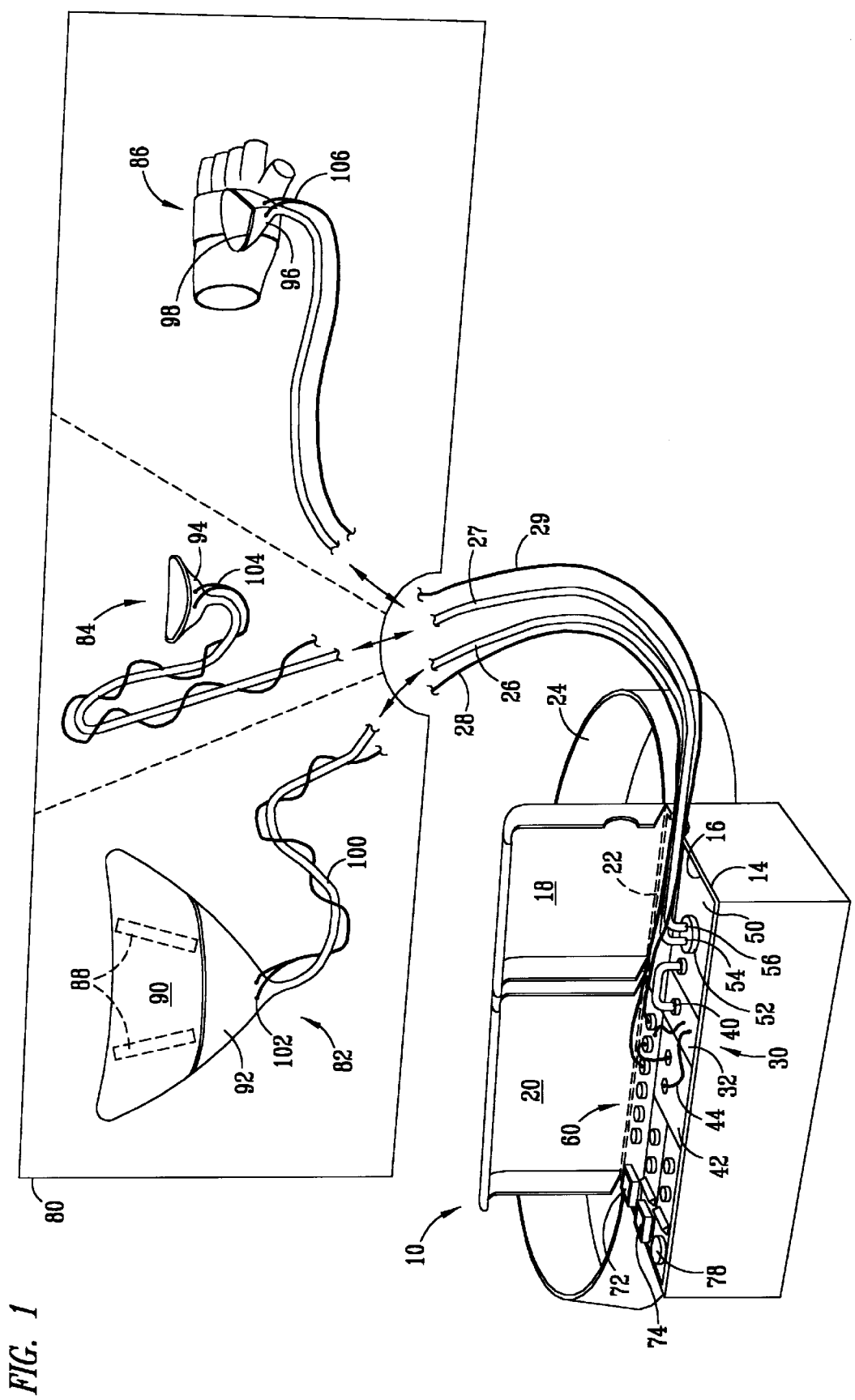
FIG. 1 is a schematic depiction of one embodiment of a portable hygienic saliva compensation device connectable to one or more of a plurality of alternative designs for a saliva collection unit, including, for example, a shirtfront unit, a face collection unit, and a wrist collection unit as shown.
Figure 2:
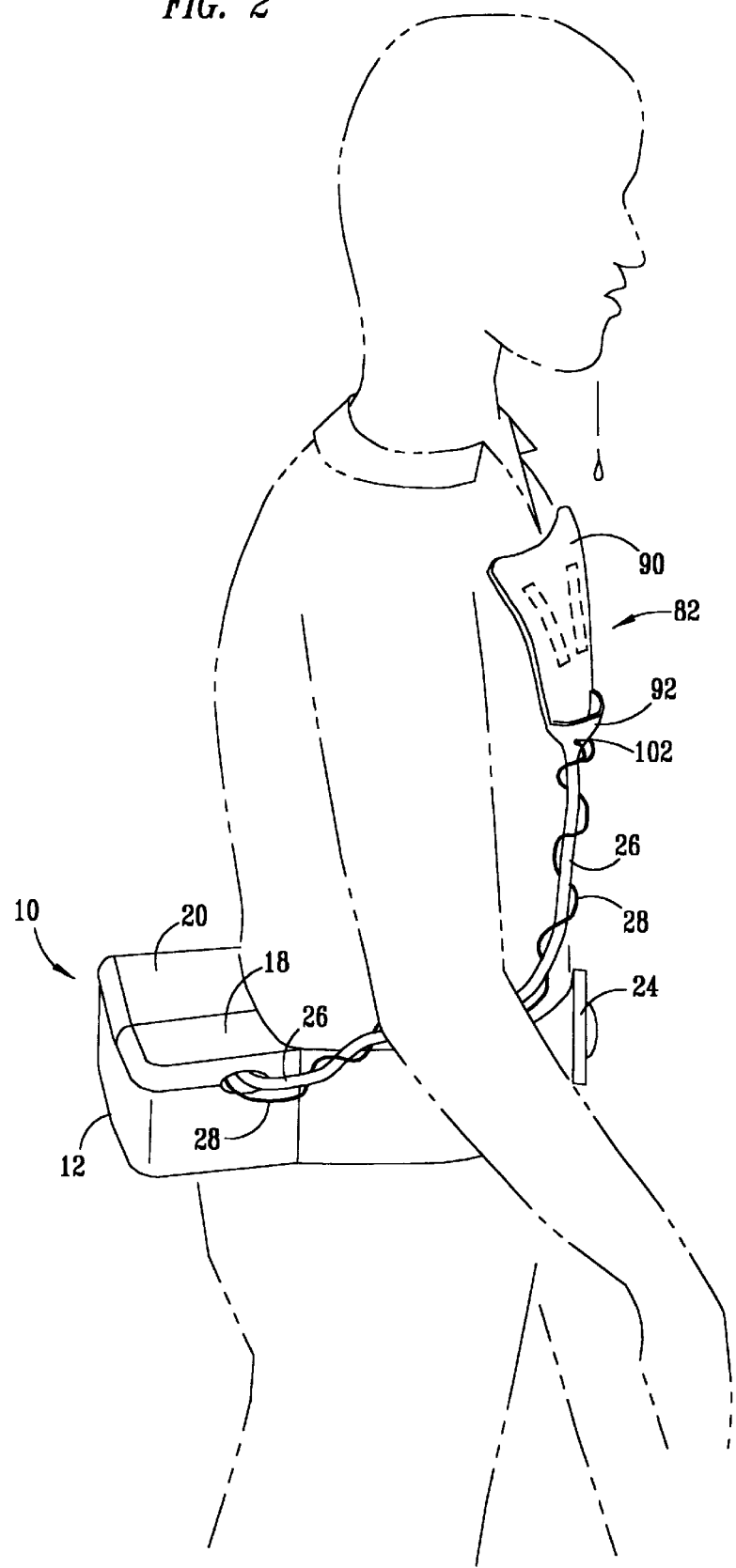
FIG. 2 is a schematic depiction of a portable fanny pack embodiment with a shirtfront collection unit in place on a user (shown in phantom lines)
Figure 3:
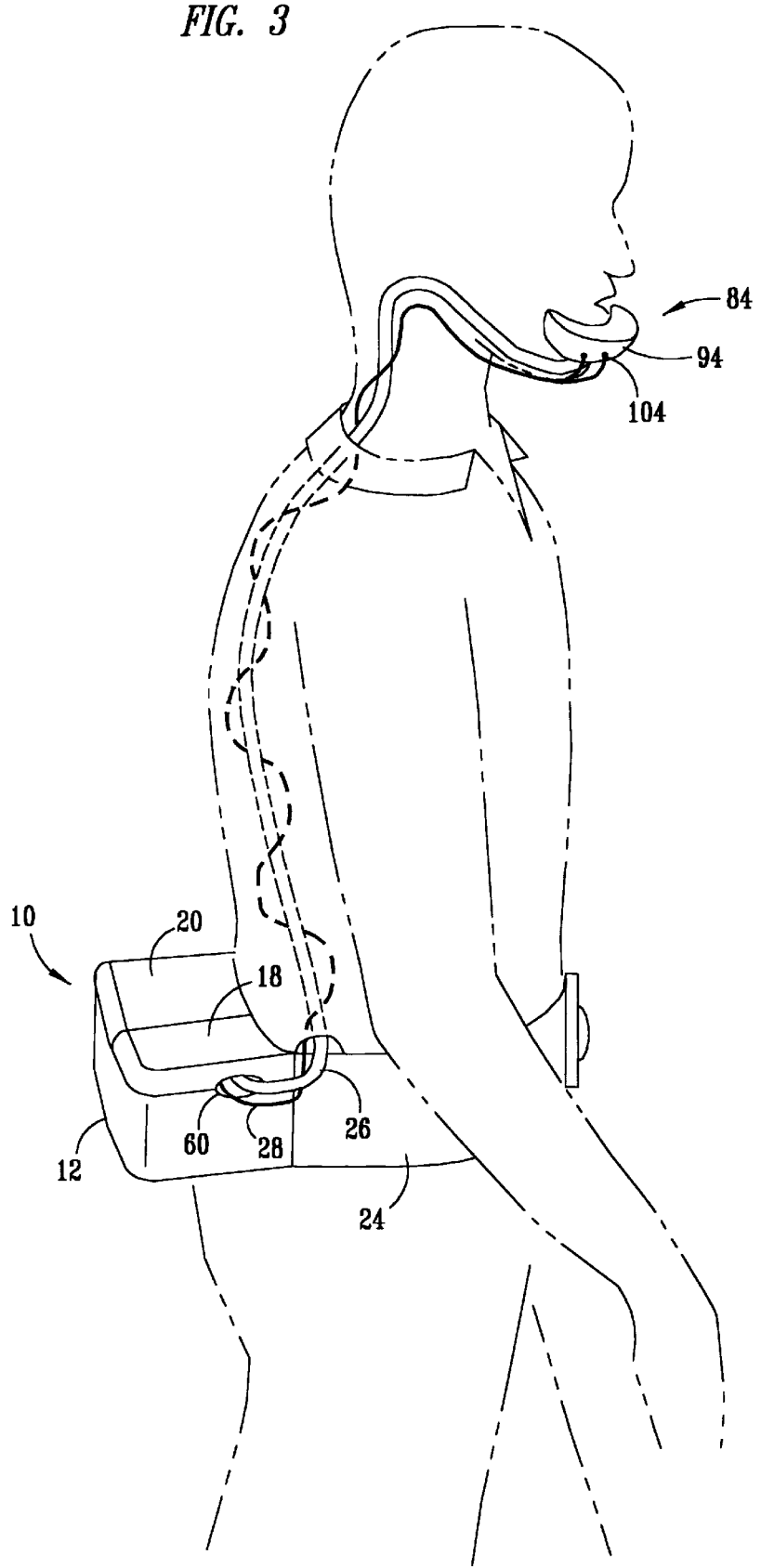
FIG. 3 is a schematic depiction of an embodiment of the invention which is a portable fanny pack modular unit and a face collection unit adhered below the lower lip of the user (shown in phantom lines)
Figure 4:
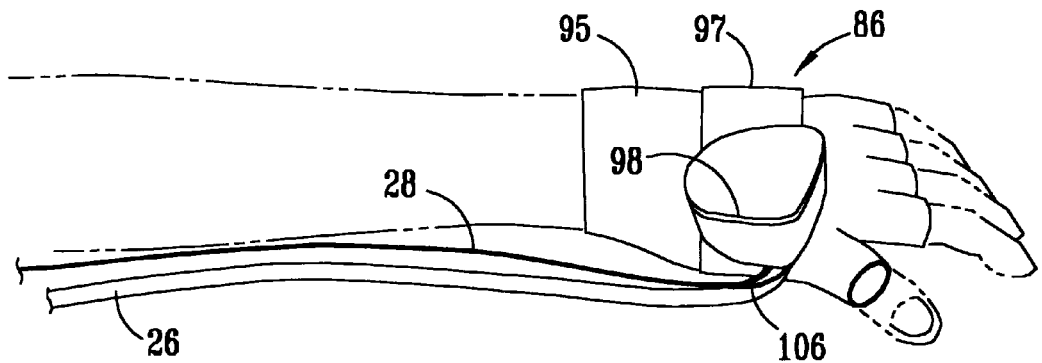
FIG. 4 is a partial schematic side view of a wrist collection unit.
Figure 5:
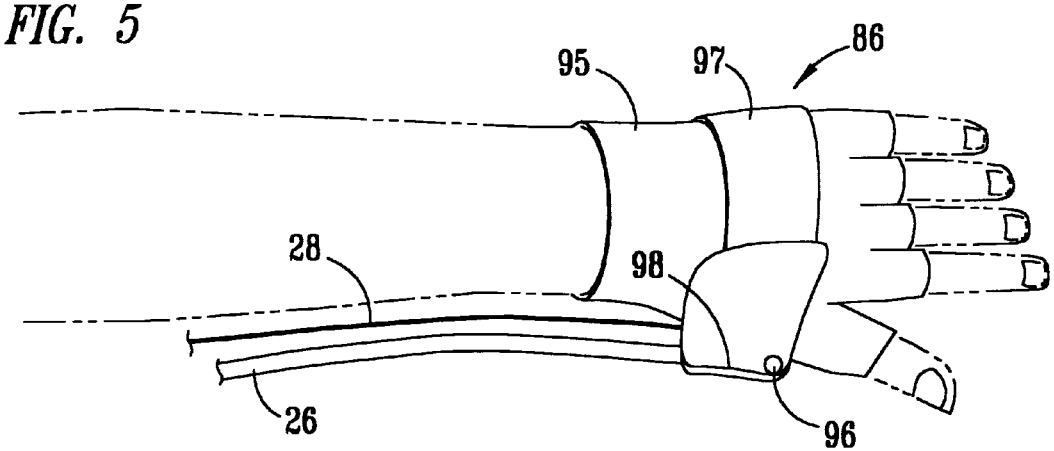
FIG. 5 is a schematic top view of the wrist collection unit of FIG. 4.

FIG. 1 is a schematic depiction of a portable hygienic saliva compensation device 10 connectable to two of three alternative designs for a saliva collection unit schematically depicted in box 80 as shirtfront unit 82, face unit 84 and wrist collection unit 86. The use of each of the selectable collection units 80 will be more fully understood and more fully described below with reference to FIGS. 2, 3 and 4 in which FIG. 2 is a schematic depiction of a portable fanny pack embodiment with a shirtfront collection unit in place on a user (shown in phantom lines); FIG. 3 is a schematic depiction of a portable fanny pack embodiment modular unit connected to a face collection unit adhered below the lower lip of the user (shown in phantom lines); FIG. 4 is a partial schematic side view of a wrist collection unit. FIG. 5 is a schematic top view of the wrist collection unit of FIG. 4.

Referring again to FIG. 1, the hygienic saliva compensation device includes a carrying case 12, the exterior of which may be made of any number of protective outer material such as fabric, polymeric material, metallic material constructed to provide an interior space 16. Preferably the is carrying case is formed of a sewn fabric material having a structural sheet material such as cardboard or polycellular material or Styrofoam interposed there along to provide both structure and protection for the components contained within the interior 16. In the embodiment depicted a two-piece cover including a reservoir cover 18 and a control cover 20 are provided pivotally-hinged or flexibly attached along a top edge along the top edge of the carrying case. A support device 24, which in the embodiment shown is a belt 24, is used for conveniently removably securing the carrying case to the user for convenient unencumbered portability. A suction tube 26 and sensor cable 28 which extends from the side of the carrying case and connects to various internal components at one end and connects to one of the selected collection units 82, 84 or 86 at the other end. Suction tube 26 connects to container 50 through inlet cap 52 and first inlet connection 54 extending through the inlet cap. Pump 32 of the pump unit 30 receives power from power cable 44 connected to battery 42. The collection container 50 is sealed and capable of withstanding at least a partial vacuum. Pump 3w of pump unit 30 connects to container 50 through a vacuum tube 34 to container 50 through a vacuum tube 34 to create a vacuum in container 50 to suction saliva through suction tube 26. In a preferred embodiment a second suction tube 27 also connects to the container 50 at second inlet 38 and for suctioning saliva from a second one of the selectable collection units 82, 84 and 86. Saliva pumped is through the second suction tube 27 and into the collection reservoir through cap 52 and second inlet tube 56.

Sensor cable 28 extends along with tube 26 and/or tube 27 from the collection unit interconnecting with one or more sensor switches 102, 104 or 106, each correspondingly attached to the lower apex of a funnel portion 92, 94 or 96 of each of the collector units 82, 84 or 86 respectively. The sensor cable 28 is selectably connectable to one of the sensors 102, 104 or 106 and thereby communicates the input from the collector to the control unit 60. Particularly advantageous is the automatic detection of moisture at the apex of the funnel of the collector unit which provides a signal to the first circuit panel 62 of the control module 60 at one of a plurality of input connectors 70. The first circuit panel 62 is also interconnected to receive power from a portable power supply such as main rechargeable battery 42 or, in the alternative, includes its own separate battery (not shown) and provides programmable control of the pump unit 30 through control wire 46. Pump 32 of pump unit 30 is activated upon the receipt of a signal from the particular sensor switch 102, 104 or 106 as is selectably attached at the opposite end of sensor cable 28 at any given time.

Control module 60 also includes a manually activatable switch 68 by which the pump may be turned on or off by the user. It will be understood that while switch 68 is depicted attached on the first circuit panel 62, it may also be a remotely operated switch positioned in a location convenient to the user such as on a handheld remove switch by which the pump 32 may be turned on or off by the user to remove saliva from the collection unit as required even in advance of sufficient accumulation to activate the sensor switch 102, 104 or 106. Inadvertent failure of such automatic sensor switch can also be accommodated by such a manual activation switch.

A plurality of input connectors 70 allow for selectable connection of multiple sensor wires and/or other sensor wires or input as from a clinical technician training console or from other sensors detecting physical or physiological activities of the user. In a preferred embodiment, the control module 60 also includes a second modular panel 64 for user cuing and a third modular panel 66 for data recordation. Additional features such as preprogrammed cuing of user activities or preprogrammed recordation of selected physiological activities of the user are thus provided to enhance the complete utility of the saliva compensation device. The basic control module also includes basic mechanisms for cuing or signaling the user to undertake certain predetermined activities and for signaling the use of the condition of the unit such as a LED light 72 provided to signal a pump "on" condition. LED light 73 signals a reservoir "full" condition and likewise various audible sound producing devices such as a speaker 74 provides remote communication capabilities or preprogrammed oral instructions to the user upon the occurrence of certain sensed conditions or events. A buzzer 76 or a unique sound producer 78, such as a "boing" sound producing device is provided to signal predetermined different actions or conditions distinguishable from the buzzer or the audible instruction for the benefit of the user.

The collection container 50 is constructed of a durable, rigid, lightweight material. It is selfcontained, sealable to maintain a vacuum, and sufficiently strong to avoid collapsing. The container 50 is constructed to be removable from carrying case 12 to provide adequate volume capacity for collecting saliva of a particular user during a predetermined period. The collection container 50 may have first and second inlet tubes 54 and 56 extending through a removable inlet cap 52 by which the reservoir may be conveniently emptied. The reservoir 60 also preferably has a level indicator 58 to detect the amount of saliva collected. Indicator 58 may be a visual graduated, transparent or translucent viewing panel, or in the alternative, may comprise a level sensing float or, in a preferred embodiment, comprises an electronic sensor device by which the control module 60 receives information concerning the level of saliva collected. The level may be detected at a full level or at predetermined increments from a first measurable amount to any of a number of preselected intermediate levels up to a fall level. A substantially continuous level indication can also be provided electronically to the control module 60. Upon reaching the full level the user will be cued or signaled to remove and empty the collection container 50 by lifting it from the carrying case, disconnecting inlet cap 52 and pouring out the contents of the container. The quantity collected can be separately and independently measured or it may be disposed of if monitoring and researching does not require additional quantity measurements.

Referring now to FIG. 2, a shirtfront collector 82 is depicted as removably attached to the user. Preferably, the attachment is directly attached to the user's shirtfront through double-sided adhesive tape 88, so that the funnel portion 92 is presented in position below a predetermined range of positions of the user's mouth and chin. Further, a vest guard portion 90 is preferably provided by which the user's shirt or chest is protected from excessive saliva. The shirtfront collector addresses the problem for users with large and uncontrolled spills at random locations. Although a neck strap 80 could be used in some situations to support the shirtfront collector, it has been found preferable in most instances to avoid neck straps. In a preferred embodiment, double-stick tape fastens the collection inlet to the user's clothing without the use of a potentially cumbersome neck strap. The user whose saliva suddenly spills from the mouth in a stream is provided with convenient compensation and collection. The vest collector is shaped like a small trough or funnel 92 and is attached to a semi-rigid plastic vest portion or guard 90 partially encircling the front of a user's neck and positioned beneath the user's face. The guard 90 preferably has a curled edge at the sides to guide the spills into a smaller and less conspicuous collection funnel 92. Preferably a clear or transparent plastic material is used, both for the guard 90 and the funnel 92 to reduce the noticeability of the device and to facilitate aesthetic appearance. When drool spills into the funnel 92, a resistance measuring fluid sensor 102 detects liquid between two spaced-apart electrodes 101 and 103 and is activated to produce an electrical signal. The suction pump 32 is turned "on" by the signal so that the saliva will be removed by suction through the apex of funnel 92 and through tube 26. The saliva is suctioned by pump 32 and redirected into reservoir 50 (not shown in FIG. 2); the upper edge of the funnel 92 is sufficiently rigid to remain open and to present a trough directly below the user's mouth and chin for the collection of excessive saliva. The rim along the edges of the guard 90 may be constructed with a hollow channel having small perforations inwardly directly toward the surface of the vest guard 90. The hollow channel may be connected to the collection tube 26 or 27, and can be provided with a partial vacuum to section saliva from along the edges.

In an alternative embodiment of a shirtfront collector, the connector is made from a large, clear, flexible sheet of vinyl that lays against the user's shirtfront. It has an attached clear flexible vinyl funnel with the collection tube and the fluid sensor at the lower apex of the funnel. The vinyl is held on the shirtfront, preferably with clear, double-sided tape. The vinyl can be customized using scissors to conform to the user's body and to cover the substantially the entire typical spill area below the user's head. The vest funnel 82 collects saliva spilling down the vinyl sheet or guard 90 or spills falling directly from the mouth of the user into the funnel in a stream. The funnel 92 directs the saliva flow to the collection tube for suction. The upper rim of the funnel may be provided with a deformable or bendable wire portion as might be provided with an embedded metallic wire for a customization of the shape of the funnel to accommodate the particular user's range of spill area. The vinyl sheet forming the vest guard 90 and the funnel are preferably coated with a low-wetting material as, for example, the solution available under the brand name Rain-X, which increases the beading and facilitates smooth flow of the thick saliva into the collection tube. The sensor switch 102 may be constructed as a resistance switch 102 by which electrodes 101 and 102 are positioned at spaced-apart locations at the apex of the funnel 92. When a predetermined amount of saliva accumulates in the apex of the funnel 92, the resistance between the sensors will be changes, thereby signaling the presence of saliva to the vacuum. This signal is received from sensor cable 28 by the control unit 60.

With reference to FIG. 3, the selection of a lip collector 84 is more fully depicted in which a face collector unit 84 is shown attached though collector tube 26 and sensor cable 28 to a control unit 10 held within a carrying case fanny pack 12. While the face collector unit may be held in position as with straps or with an operator's headset hooked around the user's ear, it has been found that a face collector 84 forming a small funnel 94 shaped like a crescent moon with the attached suction tube 26 at the lower apex of the funnel 110. The face unit is placed on the chin under the point of a typical saliva spill. It is made of a clear, flexible silicone to make it less visible on the user's lip. The silicone face collector is placed on the chin under the point of the typical saliva spill. It is made of a clear, flexible silicone and adheres to the skin with clear, two-sided medical tape available from 3M (Part No. S 1502 1522 and 9877). Fluid resistance sensors which "know" when saliva is present are located at the inlet opening of the collection tube where it connects to the lower apex of the funnel 104. The face unit is located below the lower lip of the user so that gravity assists pulling the saliva into the collection tube. The flexible silicone collector adheres to the skin of the user with clear, two-sided medical tape available from 3M as Part Nos. 1509, 1522, and 9877. The inside of the face collector is coated with a low-wetting material such as may be obtained under the brand name Rain-X to increase the beading and facilitate flow of thick saliva to the apex of the collector 104 and into the collection tube. The weight of the device is preferably well under one ounce to allow it to be connected directly to the user's face.

With reference to FIGS. 4 and 5, a wrist collector unit 86 is depicted in a side perspective view in FIG. 4 and a top perspective view in FIG. 5. The wristband collector is usable by ambulatory and non-ambulatory users with good arm and wrist control. Because of the position of the funnel at the top of the wristband, subjects with cerebral palsy or with other motor control debilitating conditions may not be able to use the wrist collector in all instances. In the embodiment depicted, the wrist collector is formed of a molded plastic having the shape of a hollow quarter wedge of a pie. The wedge is about one inch deep with the collection tube connected at a low point in the pie wedge which forms a small funnel. Resistance sensors are also located at the low point in the funnel-formed pie wedge. The molded plastic pie wedge-shaped portion is mounted onto a wristband which may be as small as a wristwatch band or as large as a fingerless glove. A detachable material such as hook-and-loop material available from Velcro allows the collector to be selectively positioned and secured anywhere on the wristband to suit the user's needs. Preferably, the shape and size of the collector cup is selectable and formable by the clinician or the user. For example, the cup may be trimmed using scissors to conform to the user's particular physical requirements. The user can scrape left-to-right or right-to-left across the chin and lip, and the collector gathers the saliva and funnels it to the collection tube where it is suctioned. The collector is coated with a low-wetting material to increase the beading and the flow of thick saliva. The wristband and the collector are preferably opaque and can be constructed in any desired color to color combinations.

The pumping unit 30 preferably includes a vacuum pump 32 which is desirably a low volume, medium vacuum, small diaphragm pump. The diaphragm pump tends to be small and to have a long life. It is simple to repair, quiet and low cost. For example, a prototype Whisper fish pump can be modified for needed suction of approximately less than about 15 inches of mercury and about 800 ml air/min. The equivalent small battery-powered diaphragm pump with equal suction and flow may require about 200 milliamps at 6 volts.

The carrying case 12 houses the electronic and pumping hardware. It contains the pump 32, tubing 26 and 27, collection reservoir 50, and sensor and switch connection jack 70 (including two fluid sensor jacks and a user switch jack), cuing devices (X-10, two device jacks, vibration unit jack, output LEDs, low battery, container full, container present, and a spare, multipurpose jack), three voice record and playback units, a buzzer, and electronics (including processor, circuitry, batteries, charging circuits and charging circuit jack). The unit is designed to assist the user in the use of the unit, in improving swallowing, and to assist clinicians in ease of programming from PCs, data collection and data and information transfer to and from other machines such as PCs. Two clinician switch jacks are provided as spare inputs for any programmable functions that clinicians may wish to include in the saliva compensation device 10. These clinician switches can be programmed to give a specific cue to the user. The collection container "present" jack and the second fluid sensing jack allow two collection devices to be used simultaneously.

Figure 6:
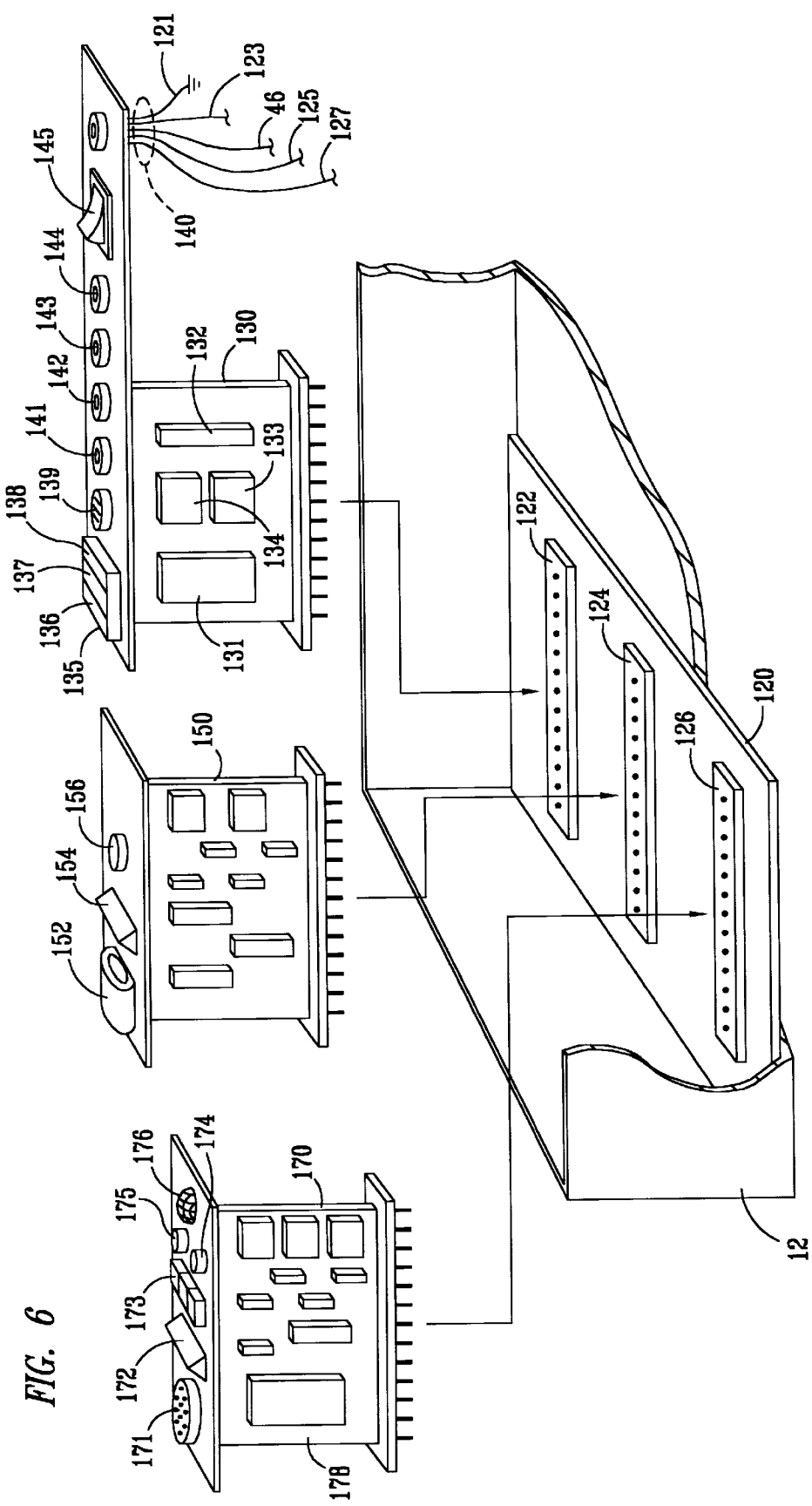
FIG. 6 is a schematic partial assembly view of electronic modular components for pin connection attachment and interconnection to a circuit board in a carrying case for interconnection with a battery power supply, activation of pump and appropriate interconnection with sensors and switching mechanisms associated with the collection units.

FIG. 6 depicts a schematic partial cutaway assembly view in which the modular components of the control unit 60 are depicted in an exploded configuration shown. A portion of the carrying case 13 is shown in cutaway view with a common power command and data busbar 120 having a basic control unit connector 122, a clinician's option board connector 124 and a voice input/output (I/0) and communications option board connector 126 are attached to the common data board appropriately interconnected therewith and with the pump and battery for receiving the basic control unit module 130, the clinician's option board 150 and the voice input/output and communications options board module 170. The basic control unit contains the processor chip 131, device interface buffer 132 and plurality of driver chips 133 and 134 (as required), as well as connections for sensory input from the machine such as a ground wire 121, a battery-connected power wire 123, a pump activation line 46, a tubing obstruction sensor 125 and a reservoir full sensor 127. A LED status display 135 preferably provides indicator sections to indicate possible "error" conditions such as ajar fall indicator 136, vacuum obstruction indicator 137, and a low battery indicator 138. An onboard buzzer 139 may also be present to provide a sound a tactile error signal corresponding to any one of the error signals provided by LED 135.

A variety of connection jacks are provided including a low voltage current jack 141 for turning on the appropriately connected remote device. A user switch jack 146 is provided to accommodate a "stereo" plug which, inserted in one side can serve as the connector to the user's pump activation switch and then connected to the reverse side serve as an external clinician's switch (useful without requiring external computer and software serial port or infrared connections). Also a first fluid sensor jack 143 is used to connect to a first fluid sensor 102, 104 or 106, and a second fluid sensor jack 144 is used for connection to a second fluid sensor switch 102, 104 or 106, depending upon the number and type of collection units 82, 84 or 86, which are being used at a given time. An on/off reset switch 145 is provided. The on/off reset switch 145 preferably is connected and preprogrammed for turning the unit on or off or, in the event the switch is transitioned from on to off to on, a reset function is performed. A battery charge jack 146 is also provided to allow the battery to be recharged in the pack without removal.

The clinician's option board 150 is an optional add-in board which provides clinician interaction and configuration, data logging, and bi-directional communication between the clinician and the control unit, as well as between the clinician and the user. When the option board is not present, a "dummy" plug (not shown) will be inserted in order to occupy the space. In one embodiment the clinician's option board will have one or more communications ports 152, a board extraction handle 154 and a physiological input connection jack 156. The communications port will allow the clinician to program an onboard PIC control microchip. The port or ports may be selected from available RS 232 ports, I$^2$C ports, infrared ports and ETC. capable of transmitting the programing information or transmitting the data as required.

The optional add-in voice input/output and communications options board 170 provides for selection of voice record and playback capabilities. Optional radio frequency communication capabilities advantageously allow remote control of electrical devices in the user's physical environment. For example, a lamp or a radio may be turned on to cue the user that it is time to swallow. It has been found that a system RF transmitter and RF receptor switch modules, known as the X-10 System available at Radio Shack, can be adapted to use as part of the combined invention for this purpose. The X-10 radio frequency transmission circuitry is mounted on the circuit board 178. There are no top-mounted elements for this part of the communication circuitry. The switch modules are plugged into household appliances. A voice output speaker 171 is usefull mounted on the top of the communications module to provide an audible voice playback function in the unit. A board extract handle 172 is provided for convenient insertion and extraction of the optional module 170. A switch (DIP) 173 is provided to select on of three voice units for record and/or playback. A record switch 174 is provided which may be a pushbutton 174 and a playback switch 175 which also may be a pushbutton 175 are provided. The record microphone 176 allows the clinician or trainer to record and play back messages for the user.

Figure 7:
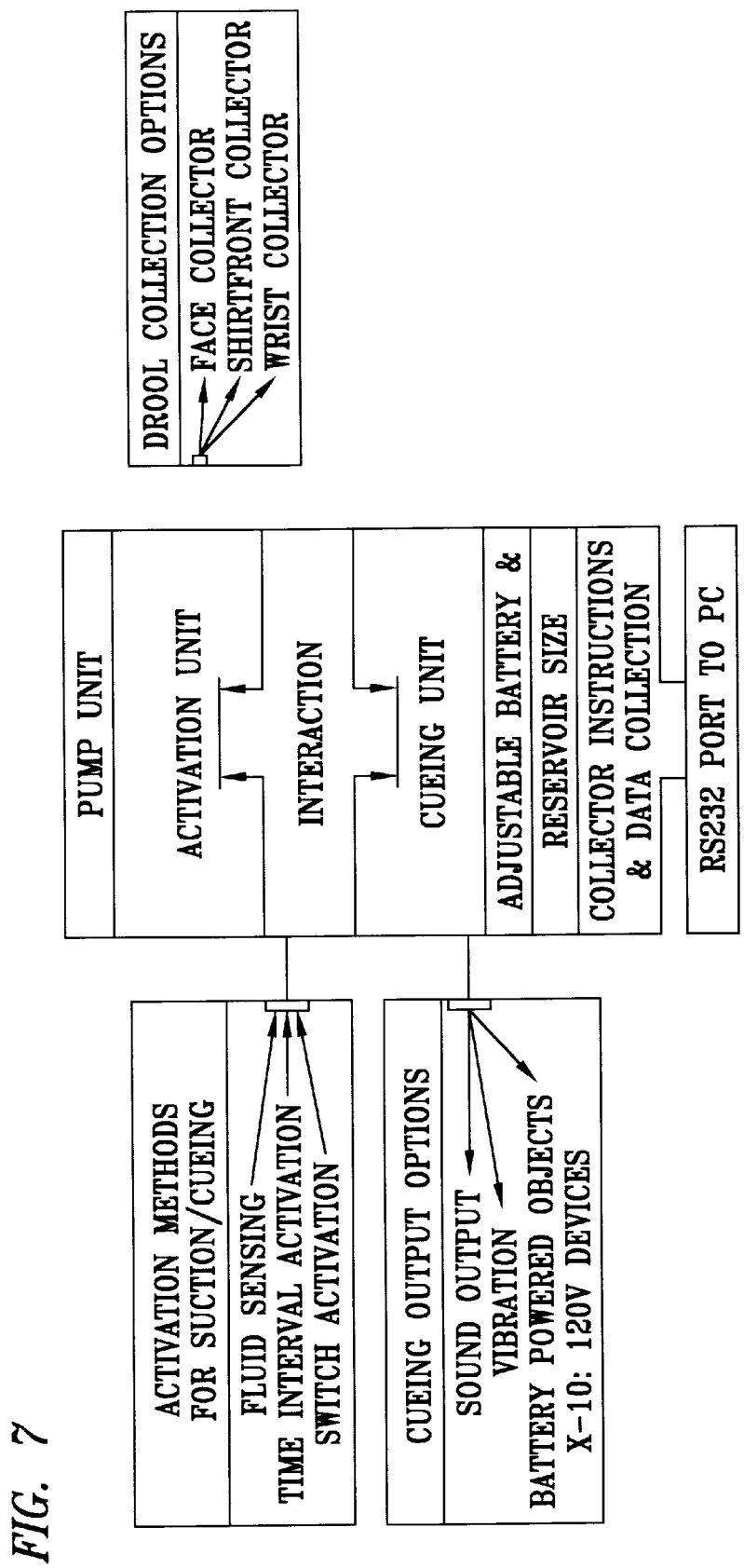
FIG. 7 is a schematic overview depiction of the modular components of the saliva compensation device, including a depiction of the pump unit, the drool collection options including face collector, shirtfront or vest collector and wrist collector, a depiction of the activation unit and activation methods for suction cuing, including fluid sensing, time interval activation, and switch activation, a depiction of the cuing unit, including cuing output options for sound output, vibration output, LED output, and environmental control using remote modules such as with any X10 system, a depiction of the power supply, a depiction of the saliva reservoir container, and a depiction of the data collection module and the communication ports for data transfer to personal computers.

FIG. 7 is a schematic depiction of the saliva compensation device including the pump unit, the activation unit, the cuing unit with interaction therebetween, adjustable battery and adjustable container size, data collection portion with an RS-232 communications port to a PC. Along with the activation unit, activation methods for suction and cuing are provided with capabilities for fluid sensing, time interval activation, and manual switch activation. The saliva collection options associated with the activation unit and the pump unit include the face collector, the shirtfront collector and the wrist collector. The cuing options associated with the cuing unit and the interaction between the cuing unit and the activation unit include sound output capabilities, vibration capabilities, battery powered accessories, and X-10 radio frequency communication.

Figure 8:
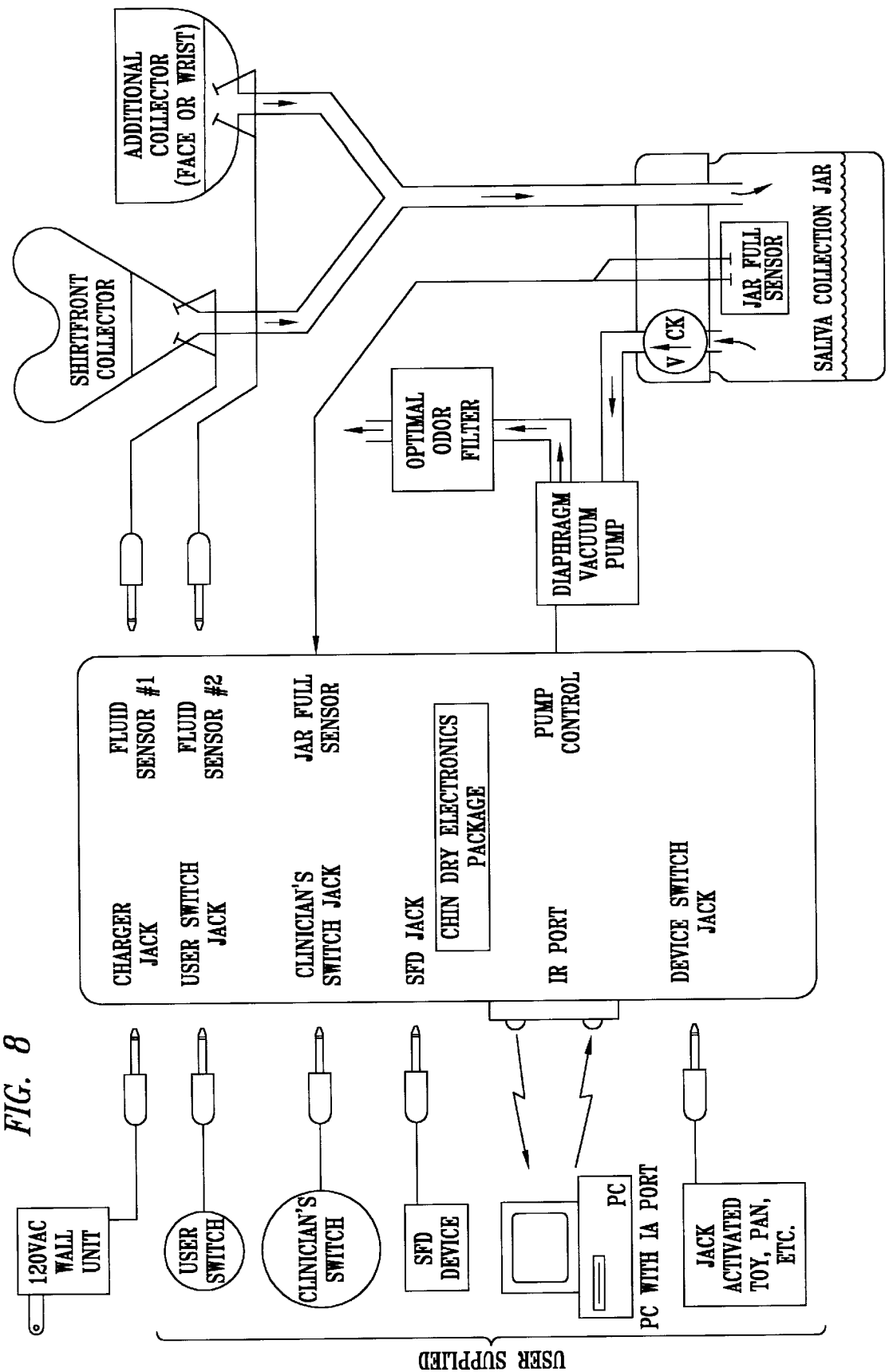
FIG. 8 is a schematic modularized system by which component parts of the saliva compensation device are detachably interconnectable with the electronic circuitry of the present invention.

FIG. 8 is a schematic depiction of the saliva compensation device 10, electronic package coupled to the various alternative components.

Figure 9:
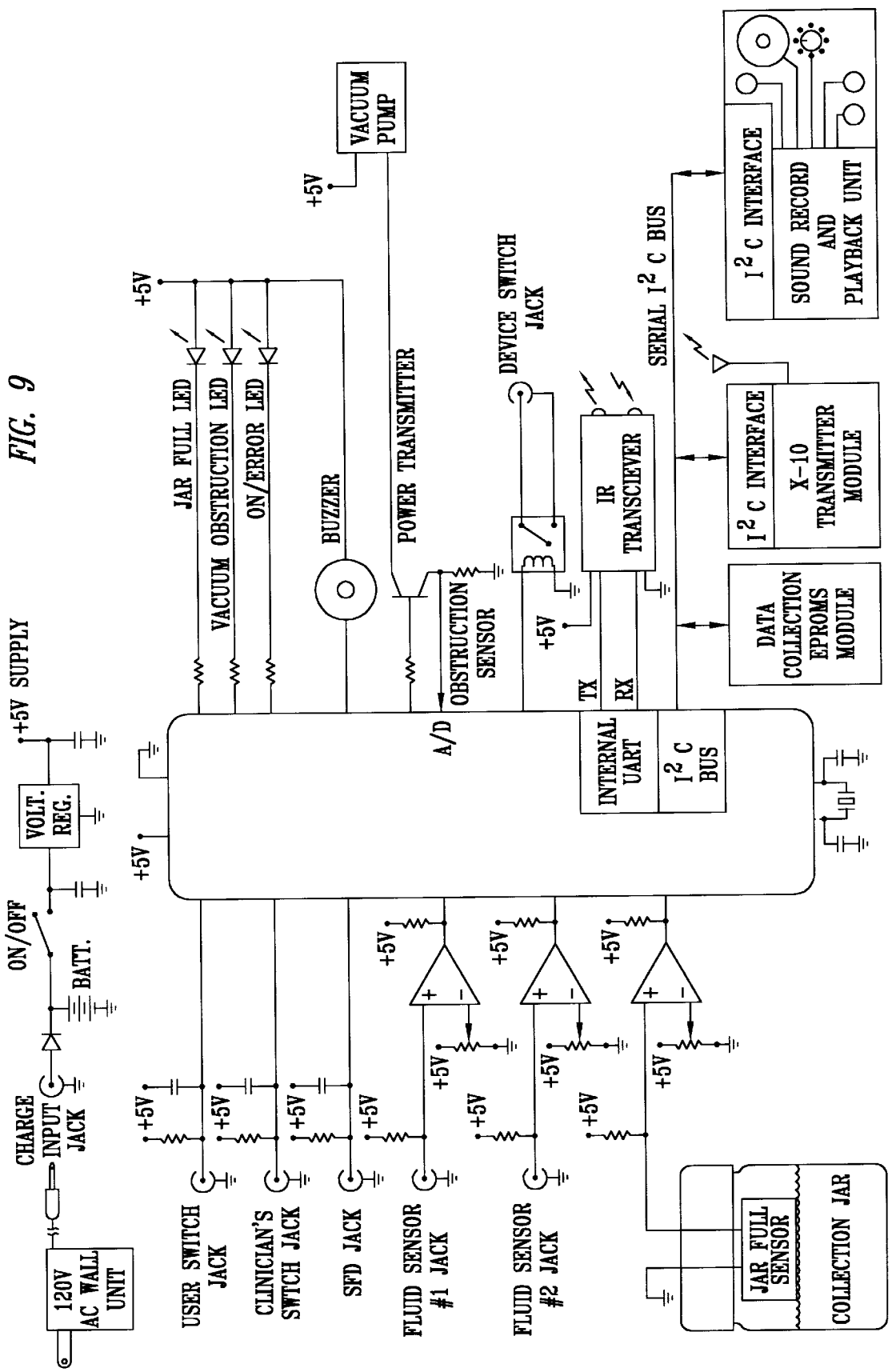
FIG. 9 is a schematic circuit diagram showing electronic circuitry interconnecting between a PIC which can be variously programmed to function as a microprocessor control chip and various components, sensors, user input, user cuing devices, pump activation, programming interface, and data transfer interfaces according to the present invention.

FIG. 9 is a schematic circuit diagram of one alternative embodiment showing electronic circuitry interconnecting between a microprocessor control chip and various components, sensors, user input, cuing devices, pump activation, clinician input/output, and data transfer interfaces according to the present invention.

Figure 10A:
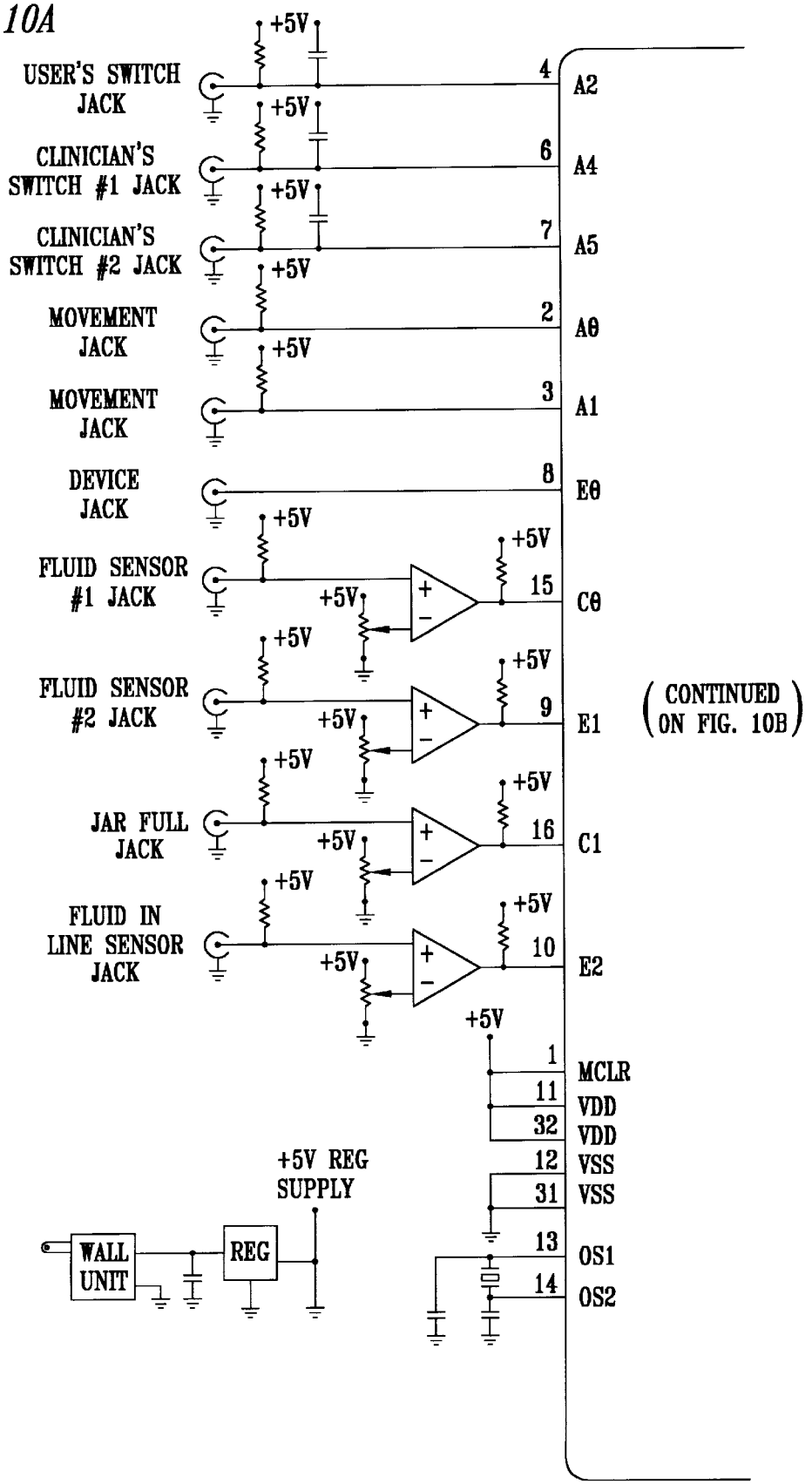
FIGS. 10A and 10B are detailed electronic circuitry and interconnection with the microprocessor chip for controlling the saliva compensation device elaborating in greater detail on the schematic of FIG. 9 according to the present invention.
Figure 10B:
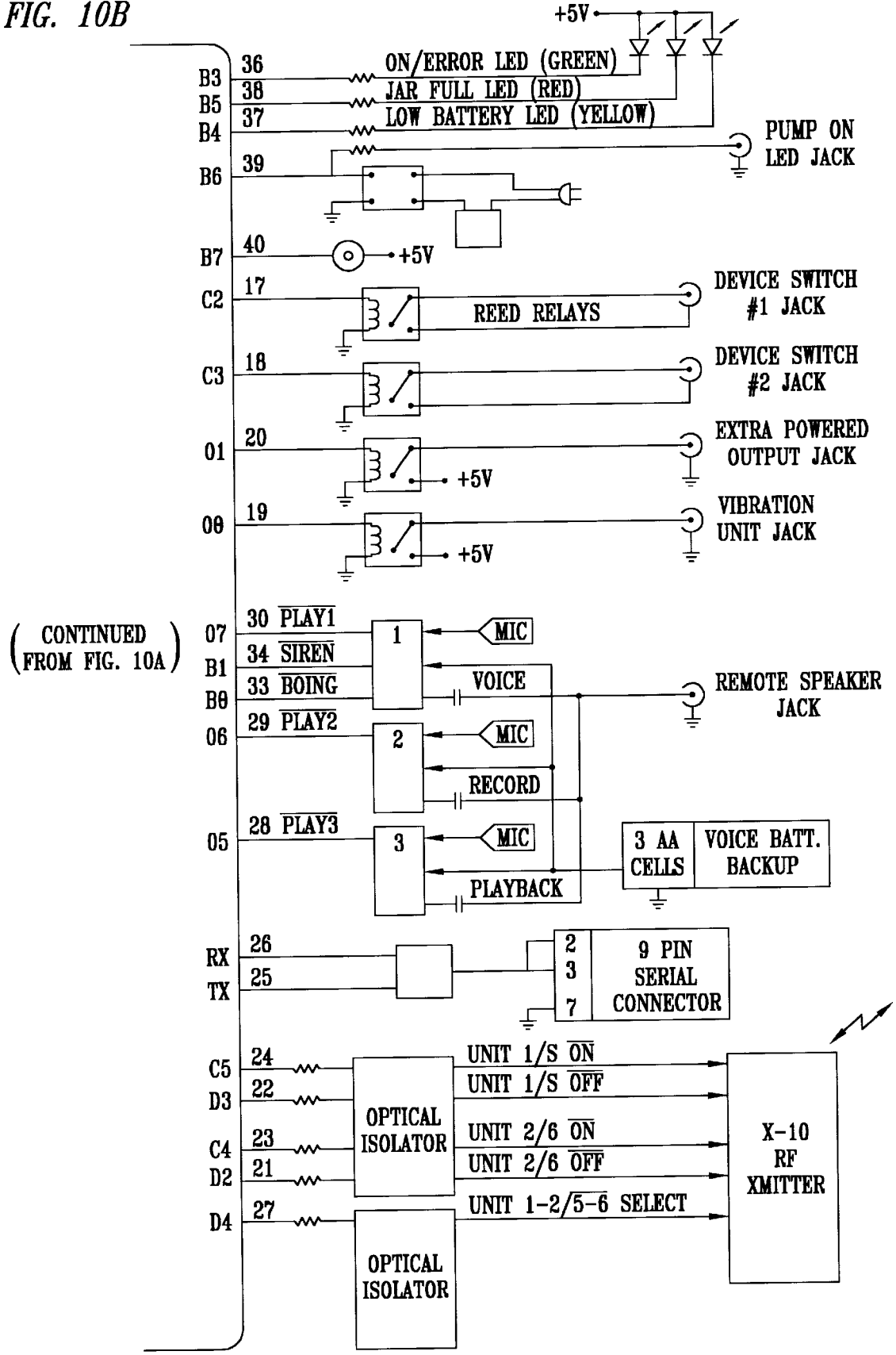

The embodiment depicted in FIGS. 10A and 10B includes two portions of a detailed electronic circuit diagram with circuitry interconnection with the microprocessor chip controlling the saliva compensation device according to the present invention. The specific features and values set forth are representative of the structural features of the invention and instructional to those skilled in the art. The specific components and values therefore are not intended to limit the scope of the invention as described and claimed.

Other alterations and modifications of the invention will likewise become apparent to those of ordinary skill in the art upon reading the present disclosure, and it is intended that the scope of the invention disclosed herein be limited only by the broadest interpretation of the appended claims to which the inventors are legally entitled.

What is claimed is:

1. A portable saliva compensation device comprising:
   a) a carrying case;
   b) a vacuum pump in said carrying case;
   c) a container in said carrying case;
   d) a portable power supply in said carrying case operatively connected to provide power to said vacuum pump;
   e) an electrical control circuit operatively connected to said portable power supply and to said pump;
   f) a saliva collection device positioned at or below a user's mouth for collecting excess saliva;
   g) a hollow tube connecting between said saliva collection device and said container; and
   h) a saliva detection switch in said saliva collection device coupled to said electrical control circuit to activate said vacuum pump when saliva is detected in said saliva collection device thereby drawing said saliva from said collection device through said hollow tube and into said container.

2. A portable saliva compensation device as in claim 1 further comprising:
   a) a programable integrated circuit (PIC) in said electrical control circuit for controlling activation of said vacuum pump; and
   b) a communication port connected to said PIC for programing said PIC from a personal computer.

3. A portable saliva compensation device as in claim 2 wherein said communications port comprises a serial port.

4. A portable saliva compensation device as in claim 2 wherein said communications port comprises a parallel port.

5. A portable saliva compensation device as in claim 2 wherein said communications port comprises an infrared port.

6. A portable saliva compensation device as in claim 1 wherein said vacuum pump comprises a lightweight diaphragm pump connected to said container for drawing a partial vacuum in said container so that the saliva is vacuumed through said collection device.

7. A portable saliva compensation device as in claim 6 wherein said container further comprises a measuring device for determining the presence of one or more predetermined volumes of collected saliva.

8. A portable saliva compensation device as in claim 7 wherein said reservoir measuring device comprises a scale formed on said container.

9. A portable saliva compensation device as in claim 7 wherein said measuring device further comprises an electronic liquid detection device attached in said container for determining one or more predetermined quantities of saliva in said container.

10. A portable saliva compensation device as in claim 9 wherein said predetermined levels detected comprise a minimum detectable level indicating the presence of saliva in said container and a maximum detectable level indicating that the container is full.

11. A portable saliva compensation device as in claim 1 wherein said carrying case comprises a fanny pack having a belt for strapping said carrying case to a user for "hands-free" carrying.

12. A portable saliva compensation device as in claim 1 wherein said collection device comprises:
  a) a vest mountable funnel having an open entrance and a narrow funnel apex;
  b) a plastic vest guard attached at said open entrance of said funnel and positioned between said funnel and said user;
  c) an attachment device for temporarily attaching said vest mountable funnel at said user's chest below said user's mouth and chin;
  d) a hollow tubing coupled between said narrow funnel apex and said container; and
  e) an activation switch connected to said control circuitry for turning on said vacuum pump to vacuum saliva from said funnel.

13. A portable saliva compensation device as in claim 12 further comprising double-stick tape attached to said vest guard between said vest guard and said user for attaching said vest mountable funnel to the shirtfront of a user below said user's mouth.

14. A portable saliva compensation device as in claim 1 wherein said collection device comprises a face mountable funnel device having a face contacting surface, a front rim and a lower apex opening in said funnel and wherein:
  a) said hollow tube is connected to said lower apex opening; and
  b) said saliva detection switch is positioned within said lower apex opening of said funnel and operatively coupled to said electrical control circuit for activating said pump when saliva is detected in said face mountable funnel and for deactivating said pump when saliva is not detected.

15. A portable saliva compensation device as in claim 14 further comprising a malleable non-toxic adhesive interposed in a layer between said face contacting surface and said user's lower lip to secure said face mountable collection funnel to said user's face.

16. A portable saliva compensation device as in claim 1 wherein said collection device comprises:
  a) a band securable to a user's wrist;
  b) a collector cup attached to said band;
  c) an opening at a corner of said collector cup;
  d) a saliva detection switch positioned in said opening and operatively connected to said electronic control circuit for activating said pump when saliva is detected in said opening; and
  e) wherein said hollow tube is connected to said opening.

17. A portable saliva compensation device as in claim 1 further comprising:
  a) another saliva collection device; and
  b) another hollow tube connected between said saliva collection device and said container for moving saliva down therein to said pump.

18. A portable saliva compensation device as in claim 1 further comprising a manual switch for manual activation of said pump.

19. A portable saliva compensation device as in claim 1 further comprising a data recordation circuit connected to said control circuit.

20. A portable saliva compensation device as in claim 19 further comprising a data transfer device by which recorded data may be transferred to a remote device such as a PC.

21. A portable saliva compensation device as in claim 16 wherein said data transfer device comprises a serial port.

22. A portable saliva compensation device as in claim 16 wherein said data transfer device comprises a parallel port.

23. A portable saliva compensation device as in claim 16 wherein said data transfer device comprises an infrared port.

24. A portable saliva compensation device as in claim 1 further comprising at least one user cuing device activatable to signal a user upon sensing a predetermined event.

25. A portable saliva compensation device as in claim 24 further comprising a plurality of cuing devices activatable to signal the user upon sensing one of a plurality of predetermined events.

26. A portable saliva compensation device as in claim 24 wherein said compensation device further comprises a radio frequency transmitter and a remote RF received switch connected to a remote electrical appliance to act as a cueing device to cue the user to take a predetermined action upon activation of said remote RF switch by said RF transmitter.

27. A portable saliva compensation device as in claim 1 wherein said electronic control is programmable to detect one or more predetermined activities or conditions of the user, of the pump, the container, and of the saliva detection switch.

* * * * *